United States Patent [19]

Ogata et al.

[11] Patent Number: 5,441,972
[45] Date of Patent: Aug. 15, 1995

[54] PHARMACEUTICAL USE OF PYRIDOXAL DERIVATIVE

[75] Inventors: Kazumi Ogata, Toyonaka; Shunji Sogo, Yao; Eri Inoue, Kobe, all of Japan

[73] Assignee: Senju Pharmaceutical Co., Ltd., Osaka, Japan

[21] Appl. No.: 222,596

[22] Filed: Apr. 4, 1994

[30] Foreign Application Priority Data

Apr. 2, 1993 [JP] Japan .................................. 5-076490

[51] Int. Cl.⁶ .............................................. A61K 31/44
[52] U.S. Cl. ...................................... 514/342; 514/912
[58] Field of Search ................................ 514/342, 912

[56] References Cited

PUBLICATIONS

*J. Am. Chem. Soc.,* vol. 70, 1948, pp. 3429–3431.
*Org. Magn. Reson.,* vol. 20, No. 3, 1982, pp. 138–140.
Chemical Abstracts, 114:164089 (1991). Faggiani et al.

*Primary Examiner*—Zohreh Fay
*Attorney, Agent, or Firm*—Sughrue, Mion, Zinn, Macpeak & Seas

[57] ABSTRACT

A novel use of the compound of the formula

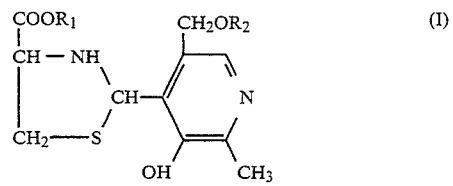

wherein $R_1$ is hydrogen atom or lower alkyl and $R_2$ is hydrogen atom or phosphoric acid group, or a pharmacologically acceptable salt thereof for preventing and treating cataract. The compounds of the formula (I) and pharmacologically acceptable salts thereof of the present invention inhibit initial changes in the lens, such as vacuolation and trochoidal change, and almost completely inhibit a decrease in the amounts of reduced glutathione and cysteine in the lens, so that they are advantageously used for the prevention of the onset and progress of cataract.

9 Claims, No Drawings

PHARMACEUTICAL USE OF PYRIDOXAL DERIVATIVE

FIELD OF THE INVENTION

The present invention relates to a pharmaceutical use of a compound of the formula (I) to be mentioned later. Specifically, the present invention relates to an anticataract agent and a method for preventing and treating cataract. More particularly, the invention relates to a useful anticataract agent comprising a compound of pyridoxal (or pyridoxal-5-phosphate) and cysteine (or its alkyl ester) bonded thereto, or a pharmacologically acceptable salt thereof, and to a method for preventing and treating cataract, comprising administering said compound or a pharmacologically acceptable salt thereof.

BACKGROUND OF THE INVENTION

Cataract is a disease in which an eyeball lens becomes opaque to result in a lowered eyesight. It is developed in humans and other animals as well. For example, an oral administration of naphthalene to a house rabbit, which makes a dependable model for human in examining pharmacological action of an anticataract agent, results in vacuolation in and trochoidal change (speichen) of a lens, which are prodomes of cataract, and the amounts of reduced glutathione and cysteine in the lens are found to decrease at this point.

Therefrom an expectation follows that the inhibition of such initial changes in the lens and the inhibition of a decrease in the amounts of reduced glutathione and cysteine in the lens at the aforementioned stage will result in effective prevention of the onset and progress of cataract.

SUMMARY OF THE INVENTION

The present inventors have conducted intensive studies with the aim of finding a compound capable of effectively preventing the onset and progress of cataract by way of the inhibition of the changes in the lens and the inhibition of the decrease in the amounts of reduced glutathione and cysteine in the lens. As a result, they have found that a compound of pyridoxal (or pyridoxal-5-phosphate) and cysteine (or its alkyl ester) bonded thereto or a pharmacologically acceptable salt thereof can satisfactorily achieve the object and completed the invention.

Accordingly, the present invention relates to a useful anticataract agent comprising a compound of the formula

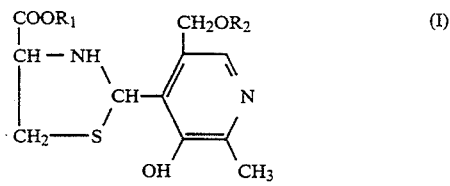

wherein $R_1$ is hydrogen atom or lower alkyl and $R_2$ is hydrogen atom or phosphoric acid group ($-PO_3H_2$), (hereinafter referred to as the Compound) or a pharmacologically acceptable salt thereof.

The present invention also relates to a method for preventing and treating cataract, comprising administering an effective amount of the aforementioned compound of the formula (I) or a pharmacologically acceptable salt thereof.

DETAILED DESCRIPTION OF THE INVENTION

The Compound to be used for the anticataract agent of the present invention has, as depicted by the foregoing formula, a chemical structure wherein pyridoxal (or pyridoxal-5-phosphate) and cysteine (or its alkyl ester) are condensed.

The lower alkyl for $R_1$ is preferably straight chain, branched chain or cyclic and has 1 to 5 carbon atoms. Examples thereof include methyl, ethyl, n-propyl, iso-propyl, cyclopropyl, n-butyl, tert-butyl, sec-butyl, n-pentyl, 1-ethylpropyl and isopentyl.

One of the elements constituting the Compound of the invention, cysteine, is a sole amino acid having an active SH group from among the amino acids constituting a protein. It is present in the living body as a free amino acid and particularly in a large amount in liver. A shortage of the other element constituting the Compound of the invention, vitamin $B_6$ (pyridoxal), is said to cause flare, desquamatory lesion and seborrheic dermatitis-like lesion in pilar scalp, eyebrow, nasolabial furrow, opisthotic part and perineum, as well as cheilitis, angular stomatitis, glossitis etc. along with anorexia, nausea, vomition, malaise and so on.

It is not known, however, that the Compound of the present invention wherein pyridoxal (or pyridoxal-5-phosphate) and cysteine (or its alkyl ester) are condensed is useful as the objective anticataract agent.

The Compound to be used as an anticataract agent is a known compound described in literatures [Ital. J. Biochem., 32(2), 92–101 (1983), Org. Magn. Reson., 20(3), 138–140 (1982), J. Biochem. (Tokyo), 81(6), 1781–1790 (1977)] and can be synthesized appropriately by known methods. For example, pyridoxal (or pyridoxal-5-phosphate) and cysteine (or its alkyl ester) are bonded by the method of Reference Example 1 or 3 to be mentioned later or by a method analogous thereto. In addition, the corresponding salt can be obtained by optionally adjusting the pH of the reaction mixture with a base such as hydroxide of sodium, potassium, calcium or magnesium or carbonate thereof, or by dissolving the Compound in an acid such as hydrochloric acid or sulfuric acid.

The Compound to be used as an anticataract agent can be used suitably for the object of the present invention whether it is a free compound or a pharmacologically acceptable salt. Examples of the salt include alkaline metal salts such as sodium salt and potassium salt; alkaline earth metal salts such as calcium salt and magnesium salt; salts of inorganic acids such as hydrochloride, sulfate and nitrate; and salts of organic acids such as acetate. Besides these, any salt can be used appropriately insofar as it is pharmacologically acceptable.

The anticataract agent of the present invention may contain one or more of the Compounds of the invention depending on the object and need.

The anticataract agent of the present invention may be used orally or parenterally (e.g. Intra venous administration, intramuscular administration, installations) for the purpose of preventing the onset and progress of cataract. The anticataract agent of the present invention can be formulated into, for example, solid preparations such as tablets, granules, powders and capsules or liquid preparations such as injections and eye drops by known methods. These preparations may contain various conventionally-used additives such as excipients, binders, thickeners, dispersing agents, reabsorption enhancers, buffers, surfactants, solubilizers, preservatives, emulsifiers, isotonizing agents, stabilizers and pH adjusting agents.

While the dose of the Compound to be contained in the anticataract agent of the present invention varies depending on the kind of the compound to be used, body weight, age and symptoms to be treated of patients, administration route and so on, it is preferably administered to an adult daily at about 1 mg—about 100 mg once by injection or at about 10 mg—about 1000 mg per oral administration several times a day. In the case of installations, an eye drop having a concentration of about 0.05–5 (w/v)% may be administered to an adult several times a day by several drops per administration.

The anticataract agent of the present invention may contain other anticataract ingredients and/or other kinds of efficacious ingredients as appropriate besides the Compound, insofar as the object of the invention is not adversely affected.

The present invention is described in detail in the following by way of Experimental Examples and Examples which are not to be construed as limiting the invention. Experimental Example 1: Inhibition of naphthalene-induced cataract in rabbits by the Compound Using house rabbits which can make dependable models in examining pharmacological action on human cataract, the cataract inhibition effect of the Compound was tested.

Test substance

Pyridoxal cysteine (abbreviated as Cys-VB$_6$)

Test method

Fifteen male white rabbits weighing 1.5 kg- 2.0 kg were grouped into normal, control and pyridoxal cysteine-administered groups and 15% naphthalene in liquid paraffin was orally administered by 10 ml/kg (1.5 g/kg) with a stomach probe to the two groups except the normal group to induce cataract. Pyridoxal cysteine (450 mg/kg) was orally administered twice in the morning and in the evening before the naphthalene administration; 1 hour before the administration; and 6, 9, 12 and 18 hours after the administration. The lens was observed 9, 12 and 24 hours after the naphthalene administration by the use of a slit lamp. After the final observation, glutathione (GSH) amount and cysteine (Cys) amount were measured by high performance liquid chromatography (HPLC).

Quantitative determination of reduced glutathione and cysteine

Immediately after the rabbits were slaughtered by an overdose of pentobarbital, lenses were extracted and the wet weight thereof was measured. One lens was homogenized with 4 ml of 5% trichloroacetic acid (TCA) containing 5 mM disodium edetate (EDTA-2Na) and centrifuged at 4° C. and 10,000 rpm for 10 minutes. To the 5-fold diluted supernatant (300 μl) were added 0.1M sodium borate $^{(a)}$ (600 μl) and 2 mg/ml ammonium 7-fluorobenzo-2-oxa-1,3-diazole-4-sulfonate (SBD-F) $^{(b)}$ (300 μl) and the mixture was stirred. After allowing to react at 60° C. for 60 minutes, the mixture was ice-cooled to terminate the reaction. The reaction mixture (10 μl) was precisely taken and the amounts of reduced glutathione and cysteine were measured by HPLC.

Note:

$^{(a)}$ 0.1M sodium borate: solution of 0.1M sodium tetraborate containing 1 mM EDTA-2Na.

$^{(b)}$ 2 mg/ml SBD-F=dissolved in 0.1M sodium borate$^{(a)}$.

[Conditions of HPLC measurement]

Column:
ODS-2 Inertsil 150×4.6 mm i.d. 5 μm
Mobile phase:
methanol:0.1M sodium phosphate (pH=6.0)4:96
Column temperature: 35° C.
Flow amount: 1.0 ml/min
Detection: excitation 385 nm, radiation 510 nm
Injection amount: 10 μm Test results The change in the lens (speichen) occurred 9 hours after the naphthalene administration in 70% of the control group, while it was lower and in 60% of the group administered with the Compound. In addition, the degree of the change in the lens was smaller in the group administered with the Compound than it was in the control group. At 24 hours after the administration, the change in the lens could be observed in 100% of the control group, while it was low and in 80% of the group administered with the Compound. At this stage again, the degree of the change in the lens was smaller in the group administered with the Compound than it was in the control group. As demonstrated, the Compound was confirmed to suppress the change in the lens caused by the naphthalene administration.

The measurement results of the reduced glutathione and cysteine in the lens after about 26 hours from the naphthalene administration are shown in Table 1 and Table 2. As is evident from Table 1 and Table 2, the Compound almost completely inhibited the decrease in the amounts of the reduced glutathione and cysteine, thus proving its usefulness as an anticataract agent.

TABLE 1

| Group | GSH (μmol/g lens) | GSH level (%) | |
|---|---|---|---|
| Normal | 9.96 ± 1.03 | — | (n = 7) |
| Control | 7.05 ± 1.07 | 70.78 ± 10.76 | (n = 10) |
| Cys-VB$_6$-administered group | 9.61 ± 0.64 | 96.49 ± 6.46 | (n = 10) |

TABLE 2

| Group | Cys (μmol/g lens) | Cys level (%) | |
|---|---|---|---|
| Normal | 0.37 ± 0.06 | — | (n = 7) |
| Control | 0.27 ± 0.05 | 74.29 ± 12.62 | (n = 10) |
| Cys-VB$_6$-administered group | 0.45 ± 0.07 | 122.90 ± 18.46 | (n = 10) |

| Injection | |
|---|---|
| Pyridoxal-5-phosphate cysteine | 1.0 g |
| Sodium chloride | 0.8 g |
| 1N-sodium hydroxide | appropriate amount |
| sterile distilled water | appropriate amount |
| | 100 ml (pH 6.0) |

The above ingredients were mixed, sterilized by filtration, charged in a glass ampoule by 2 ml and heat-sealed to give an injection.

| Tablet | |
|---|---|
| Pyridoxal ethyl cysteine | 100 mg |
| Lactose | 80 mg |
| Starch | 19 mg |

-continued

| Tablet | |
|---|---|
| Magnesium stearate | 1 mg |

The above ingredients were mixed by a conventional method and prepared into one tablet. Sugar coating may be applied on demand.

EXAMPLE 3

| Eye drop | |
|---|---|
| Pyridoxal cysteine | 100 mg |
| Sodium chloride | 700 mg |
| Boric acid | 400 mg |
| Methyl p-hydroxybenzoate | 2 mg |
| Chlorobutanol | 30 mg |
| 1N-sodium hydroxide | appropriate amount |
| sterile distilled water | appropriate amount |
| | 100 ml (pH 5.7) |

Using the above ingredients, an eye drop was prepared by a conventional method.

Methods for synthesizing the Compound are given in the following as Reference Examples.

Reference Example 1

Synthesis of pyridoxal cysteine ($R_1=R_2=H$)

Pyridoxal hydrochloride (2.7 g) and L-cysteine (1.6 g) were dissolved in water (40 ml). Thereto was dropwise added a 10% sodium hydroxide solution to make the pH 4.5. The mixture was left standing at a cool place to allow precipitation of white crystals. The crystals were collected by filtration and dissolved in 1N hydrochloric acid for recrystallization. The solution was adjusted to pH 5.0 with 1N sodium hydroxide to allow precipitation of white needle crystals. The crystals were collected by filtration, washed with water and dried under reduced pressure at 40° C. to give 1.8 g of pale yellow crystals, m.p. 135° C. (decomposition).

Reference Example 2

Synthesis of pyridoxal ethyl cysteine ($R_1=C_2H_5$, $R_2=H$)

In the same manner as in Reference Example 1 except using pyridoxal hydrochloride (1.6 g) and ethyl cysteine hydrochloride (1.8 g), white crystals were obtained. Recrystallization from methanol-water afforded 2.3 g of white needle crystals, m.p. 112° C.–113° C. (decomposition).

Reference Example 3

Synthesis of pyridoxal-5-cysteine phosphate ($R_1=H$, $R_2=PO_3H_2$)

Water (100 ml) was added to pyridoxal-5-phosphate monohydrate (2.6 g) and L-cysteine (1.3 g), and the mixture was stirred at 50° C. to dissolve pyridoxal-5-phosphate with the progress of the reaction. After 10 minutes from the dissolution, the mixture was concentrated under reduced pressure and methanol was added thereto. The resultant yellow crystals were collected by filtration and recrystallized from methanol-water to give 2.4 g of yellow crystals. The crystals were eluted through Sephadex G-10 (trademark) with water:methanol=1:1 and yellow portions were collected to give the objective compound having a high purity.

The compounds of the formula (I) and pharmacologically acceptable salts thereof of the present invention inhibit initial changes in the lens, such as vacuolation and trochoidal change, and almost completely inhibit a decrease in the amounts of reduced glutathione and cysteine in the lens, so that they are advantageously used for the prevention of the onset and progress of cataract.

What is claimed is:

1. A method for preventing and treating cataract, comprising administering an effective amount of a compound of the formula (I)

$$\begin{array}{c} COOR_1 \\ | \\ CH-NH \\ | \quad\quad\ \ \backslash \\ \quad\quad\quad CH- \\ | \quad\quad\ \ / \\ CH_2--S \end{array} \begin{array}{c} CH_2OR_2 \\ \diagup\diagdown \\ \quad\quad N \\ \diagdown\diagup \\ OH\quad CH_3 \end{array} \quad (I)$$

wherein $R_1$ is a hydrogen atom or a lower alkyl and $R_2$ is a hydrogen atom or a phosphoric acid group, or a pharmacologically acceptable salt thereof.

2. An anticataract composition comprising a compound of the formula (I)

$$\begin{array}{c} COOR_1 \\ | \\ CH-NH \\ | \quad\quad\ \ \backslash \\ \quad\quad\quad CH- \\ | \quad\quad\ \ / \\ CH_2--S \end{array} \begin{array}{c} CH_2OR_2 \\ \diagup\diagdown \\ \quad\quad N \\ \diagdown\diagup \\ OH\quad CH_3 \end{array} \quad (I)$$

wherein $R_1$ is a hydrogen atom or a lower alkyl and $R_2$ is a hydrogen atom or a phosphoric acid group, or a pharmacologically acceptable salt thereof, and a pharmacologically acceptable excipient.

3. The anticataract composition of claim 2, which is in the form of an injection.

4. The anticataract composition of claim 2, which is in the form of tablet, granule, powder or capsule.

5. The anticataract composition of claim 2, which is in the form of an eye drop.

6. The anticataract composition of claim 5, comprising the compound of formula (I) or a pharmacologically acceptable salt thereof in a proportion of from about 0.05 w/v % to about 5 w/v %.

7. The method of claim 1, wherein the compound of formula (I) or a pharmacologically acceptable salt thereof is administered orally, intravenously, intramuscularly or by instillation.

8. The method of claim 1, wherein about 1 mg—about 100 mg of the compound of formula (I) or a pharmacologically acceptable salt thereof is administered daily by injection.

9. The method of claim 1, wherein about 10 mg—about 1000 mg of the compound or a pharmacologically acceptable salt thereof is orally administered per administration.

* * * * *

UNITED STATES PATENT AND TRADEMARK OFFICE
CERTIFICATE OF CORRECTION

PATENT NO.   : 5,441,972
DATED        : August 15, 1995
INVENTOR(S)  : OGATA et al.

It is certified that error(s) appears in the above-identified patent and that said Letters Patent is hereby corrected as shown below:

Column 4, line 11, change "$\mu m$" to --$\mu l$--;

line 52, insert --EXAMPLE 1--;

line 64, insert --EXAMPLE 2--.

Signed and Sealed this

Thirteenth Day of February, 1996

*Attest:*

BRUCE LEHMAN

*Attesting Officer*  *Commissioner of Patents and Trademarks*